United States Patent
Satoh et al.

(10) Patent No.: US 7,631,535 B2
(45) Date of Patent: Dec. 15, 2009

(54) METHOD OF CONFIRMING RECEPTION OF DROPS OF WATER AND POWDER USED FOR THE METHOD

(75) Inventors: Motoaki Satoh, Anjo (JP); Kouhei Yamada, Oobu (JP)

(73) Assignee: Denso Corporation, Kariya (JP)

( * ) Notice: Subject to any disclaimer, the term of this patent is extended or adjusted under 35 U.S.C. 154(b) by 401 days.

(21) Appl. No.: 11/656,435

(22) Filed: Jan. 23, 2007

(65) Prior Publication Data
US 2007/0169534 A1    Jul. 26, 2007

(30) Foreign Application Priority Data
Jan. 26, 2006  (JP) .............................. 2006-017818
Nov. 15, 2006  (JP) .............................. 2006-309298

(51) Int. Cl.
*G01N 27/00*    (2006.01)
(52) U.S. Cl. .................. 73/1.06; 205/788.5; 252/408.1
(58) Field of Classification Search .................. 73/1.06, 73/23.31, 31.05; 116/206; 205/788.5; 252/408.1
See application file for complete search history.

(56) References Cited

U.S. PATENT DOCUMENTS 4,902,401 A * 2/1990 Lin et al. ..................... 204/427
2003/0159928 A1  8/2003 Kojima et al. ............... 204/408

FOREIGN PATENT DOCUMENTS

JP    2003-322632    11/2003

* cited by examiner

*Primary Examiner*—Thomas P Noland
(74) *Attorney, Agent, or Firm*—Nixon & Vanderhye, PC

(57) ABSTRACT

A method of confirming reception of a drop of water has the steps of applying a powder on a surface of a gas sensing element, placing the element in a gas passage so as to expose the surface of the element to the gas passage, causing a measured gas to flow through the gas passage, receiving drops of water included in the measured gas on limited areas of the surface of the element such that the drops of water take out the powder applied on the limited areas from the element, and confirming the reception of the drops of water on the surface of the element. The powder has a melting point or a sublimation temperature equal to or higher than 1000° C.

12 Claims, 3 Drawing Sheets

METHOD OF CONFIRMING RECEPTION OF DROPS OF WATER AND POWDER USED FOR THE METHOD

CROSS-REFERENCE TO RELATED APPLICATION

This application is based upon and claims the benefit of priority of the prior Japanese Patent Application 2006-017818 filed on Jan. 26, 2006, and the prior Japanese Patent Application 2006-309298 filed on Nov. 15, 2006 so that the contents of which are incorporated herein by reference.

BACKGROUND OF THE INVENTION

1. Field of the Invention

The present invention relates to a method wherein reception of drops of water on a surface of a gas sensing element in a gas sensor is confirmed to estimate receiving conditions of the drops of water and a water confirming powder used for the method.

2. Description of Related Art

As is well known, a gas sensor is disposed in an exhaust system of an internal combustion engine of a vehicle or the like. This sensor has a gas sensing element exposed to an exhaust gas of the exhaust system and detects a concentration of a specific component (e.g., $O_2$, NO, CO or the like) of the exhaust gas.

The gas sensing element has a plate-shaped solid electrolyte body having a high mobility for oxygen ions, a gas measurement electrode disposed on one surface of the solid electrolyte body, and a reference gas electrode disposed on the other surface of the solid electrolyte body. The measures gas electrode is exposed to the exhaust gas to be measured, and the reference gas electrode is exposed to a reference gas. The temperature of the exhaust gas reaches almost 1000° C. Further, to activate the solid electrolyte body, the solid electrolyte body is heated by a heater so as to be maintained in an activity temperature range.

During the operation of the engine, moisture included in the exhaust gas adheres to limited areas of an outer surface of the gas sensing element as drops of water, so that the temperature at the surface areas of the element receiving the drops of water is considerably lowered. Therefore, a large difference in temperature is generated between each limited area and a surface area surrounding the limited area, and thermal stress is caused in the element by the temperature difference. In this case, there is a high probability that cracks occur in the element due to this thermal stress.

To prevent the occurrence of cracks, Published Japanese Patent First Publication No. 2003-322632 discloses a testing method of tentatively receiving drops of water on a surface of a gas sensing element and confirming the reception of the drops of water to estimate receiving conditions of the drops of water. More specifically, in this testing method, carbon particles are applied to or coated on the whole surface of a gas sensing element, the element is attached to a gas sensor, and the gas sensor is disposed in an exhaust system of an internal combustion engine of a motorcar. Thereafter, the engine is tentatively operated so as to output an exhaust gas, and drops of water are attached to the surface of the element. When a drop of water is attached to a limited area of the surface of the element, carbon particles applied to the limited area are removed, and a confirmative trace of receiving the drop of water is formed on the limited area. After the operation of the engine is finished, confirmative traces of the drops of water formed on the surface of the element are observed with an operator's eye, and the reception of the drops of water is confirmed. Therefore, receiving conditions (positions, sizes and the like) of the drops of water can be estimated, and the element can be modified so as to prevent the occurrence of cracks.

However, the carbon particles are burned away in a temperature range from 400 to 500° C., while the exhaust gas output from the engine has a temperature of almost 1000° C. when the engine is actually operated for a long time to operate the car. Therefore, when it is intended to confirm the reception of drops of water in the gas sensing element under the same circumstances as those in which the element is exposed to the exhaust gas of almost 1000° C. in the actually-operated engine, there is a high probability that the carbon particles applied on the surface of the gas sensing element are burned up and disappeared. In this case, even though the gas sensing element receives drops of water, it is impossible to confirm the reception of the drops of water. That is, it is difficult to estimate receiving conditions of the drops of water under the same circumstances as those obtained in an actual operation of the engine.

SUMMARY OF THE INVENTION

An object of the present invention is to provide, with due consideration to the drawbacks of the conventional method of confirming reception of drops of water, a method wherein reception of a drop of water on a surface of a gas sensing element is reliably confirmed even in the same circumstances as those obtained in an actual operation of an engine. Further, the object of the present invention is to provide a water confirming powder used for the method.

According to a first aspect of this invention, the object is achieved by the provision of a method of confirming reception of a drop of water, comprising the steps of applying a water confirming powder on a surface of a gas sensing element for detecting a concentration of a specific component included in a measured gas, placing the gas sensing element in a gas passage so as to expose the surface of the gas sensing element to the gas passage, causing the measured gas to flow through the gas passage, receiving a drop of water included in the measured gas on a limited area of the surface of the gas sensing element such that the drop of water takes out the water confirming powder from the limited area, and confirming the reception of the drop of water on the surface of the gas sensing element, based on a trace of the drop of water at which the powder is taken out. The water confirming powder has a melting point or a sublimation temperature equal to or higher than 1000° C.

The gas sensing element is used to detect a concentration of a specific component included in a measured gas. During the detection of a concentration of the specific component, the gas sensing element is exposed to a measured gas output from an engine, and the temperature of the measured gas is almost equal to 1000° C. When a drop of water included in the measured gas is attached to the surface of the gas sensing element, there is probability that cracks occur in the gas sensing element. To prevent the occurrence of cracks, the reception of the drop of water is confirmed in this method.

Because the water confirming powder has a melting point or a sublimation temperature equal to or higher than 1000° C., the water confirming powder can stably keep adhering to the surface of the element even when the gas sensing element is exposed to the measured gas of almost 1000° C. in the same circumstances as those obtained in an actual operation of an engine. Therefore, when a drop of water takes out the water confirming powder from a limited area of the surface of the gas sensing element, the reception of the drop of water can be reliably confirmed, and receiving conditions (position, size and the like) of the drop of water can be estimated. Further, the gas sensing element can be modified on the basis of the estimated receiving conditions so as to prevent the occurrence of cracks in the gas sensing element.

According to a second aspect of this invention, the object is achieved by the provision of a water confirming powder, characterized in that a water confirming powder is applied on a surface of a gas sensing element which detects a concentration of a specific component included in a measured gas, the water confirming powder is taken out from a limited area of the surface of the gas sensing element in response to a reception of a drop of water included in the measured gas on the limited area so as to obtain a confirmative trace of receiving the drop of water, and the water confirming powder has a melting point or a sublimation temperature equal to or higher than 1000° C.

Therefore, the water confirming powder can be used for the method.

BRIEF DESCRIPTION OF THE DRAWINGS

FIG. 3 is a sectional view taken substantially along line A-A of. FIG. 2; and

DETAILED DESCRIPTION OF THE PREFERRED EMBODIMENTS

Embodiments of the present invention will now be described with reference to the accompanying drawings. However, these embodiments should not be construed as limiting the present invention to structures of those embodiments, and the structure of this invention may be combined with that based on the prior art.

Embodiment 1

Figure 1:
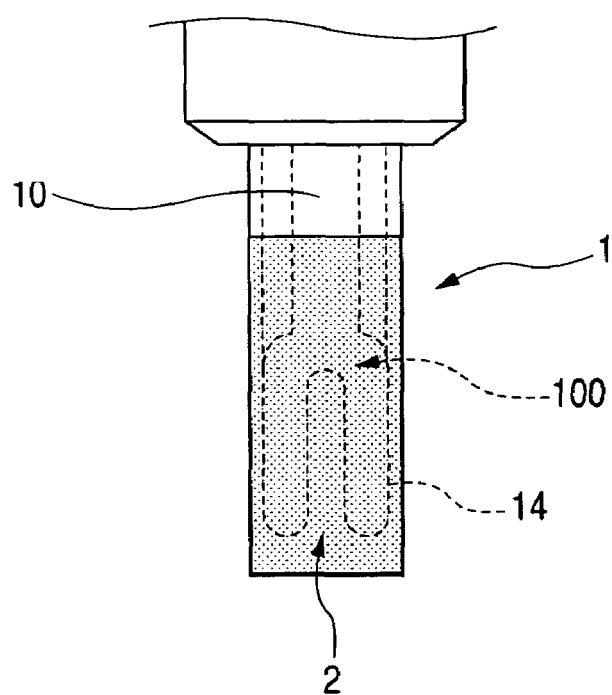
FIG. 1 is a side view of a distal portion of a gas sensing element and a water confirming powder of fine particles applied on or attached to a whole surface of the distal portion of the gas sensing element, according to the first embodiment of the present invention.
Figure 2:
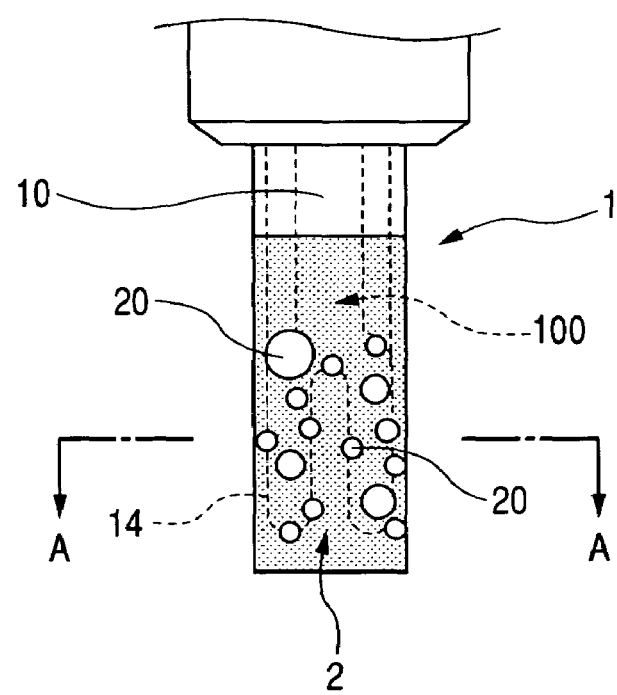
FIG. 2 is a side view of the distal portion of the gas sensing element after the tentative reception of drops of water.
Figure 3:
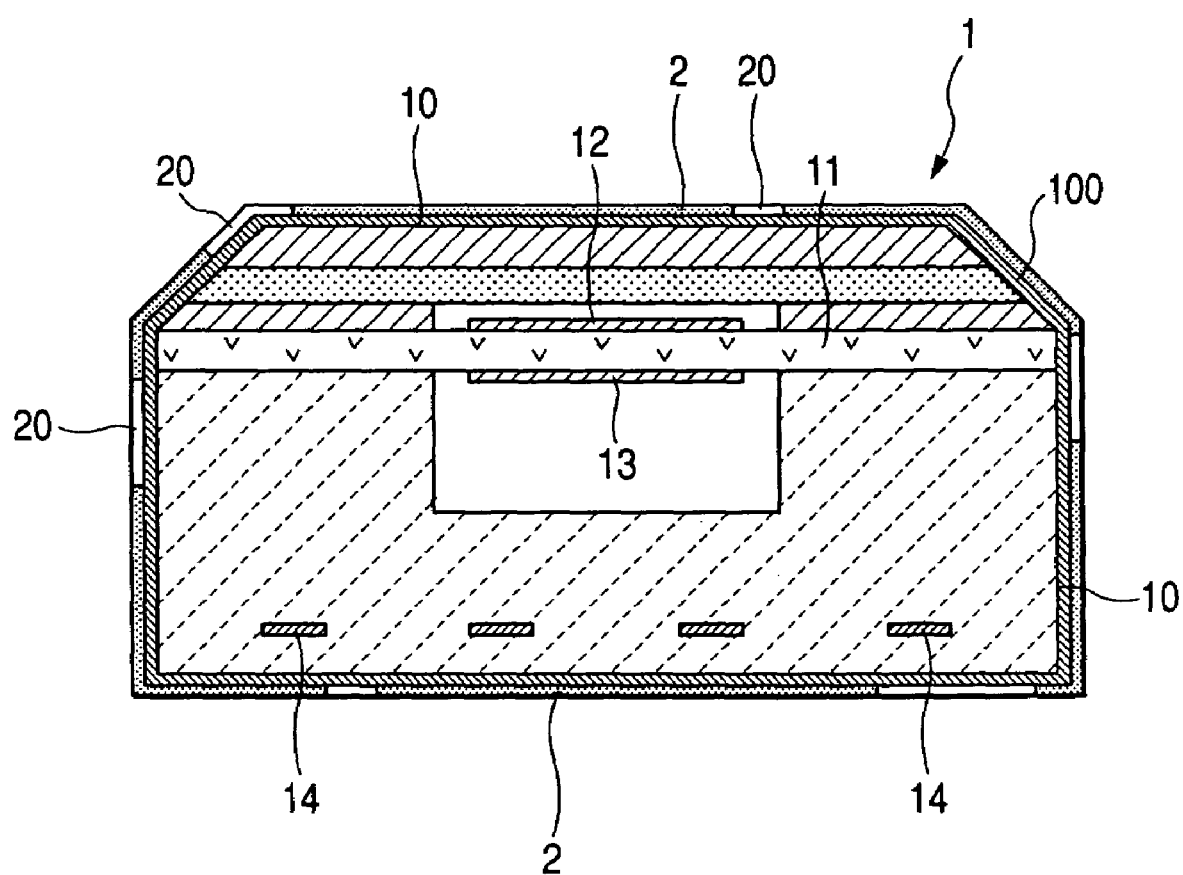

A testing method for tentatively confirming reception of drops of water on a surface of a gas sensing element and a water confirming powder of fine particles used for the testing method are described according to this embodiment with reference to FIGS. 1 to 3.

FIG. 1 is a side view of a distal portion of a gas sensing element and a water confirming powder of fine particles applied on or attached to a whole surface of the distal portion of the gas sensing element, according to the this embodiment of the present invention. FIG. 2 is a side view of the distal portion of the gas sensing element after the tentative reception of drops of water. FIG. 3 is a sectional view taken substantially along line A-A of FIG. 2.

As shown in FIGS. 1 to 3, a gas sensing element 1 has a solid electrolyte body 11 having a high mobility for oxygen ions, a gas measurement electrode 12 disposed on one surface of the solid electrolyte body 11, a reference gas electrode 13 disposed on the other surface of the solid electrolyte body 11, and a heater 14 for heating up the element 1 to an activate temperature of the element 1. The electrode 12 is exposed to a measure gas mixture, and the electrode 13 is exposed to a reference gas. Oxygen ions of the measure gas mixture or the reference gas smoothly passes through the body 11 heated to the activate temperature from one of the electrodes to the other electrode so as to generate an electric potential difference between the electrodes 12 and 13. The element 1 further has a porous layer 100 on an outer surface 10 of the element 1. The layer 100 is formed of particles made of a ceramic material such as alumina, zirconia or the like.

The gas sensing element 1 is adapted and planned to be disposed in a gas sensor (not shown). The element 1 is used as an oxygen sensing element, an $NO_x$ sensing element, an air-to-fuel sensing element or the like. In cases where the element 1 is used to detect a concentration of a specific component of a measured gas, the gas sensor with the element 1 is disposed in an exhaust system of an internal combustion engine (not shown) of a vehicle or the like, and the element 1 is heated by the heater 14 to the activate temperature. When an exhaust gas output from the engine flows through the exhaust system during the operation of the engine and reaches the electrode 12, the exhaust gas is decomposed on the electrode 12 so as to generate oxygen ions. The ions passes through the electrolyte body 11, so that an electric potential difference is generated between the electrodes 12 and 13. Then, a concentration of a specific component (e.g., $O_2$, NO, CO or the like) included in the exhaust gas is detected from the electric potential difference. The exhaust gas represents the measured gas.

However, because the exhaust gas inevitably includes moisture, this moisture adheres or is attached to limited areas of the surface 10 of the element 1 as drops of water. Further, because the element 1 is heated by the heater 14, a large difference in temperature is generated between each limited area of the surface 10 and an area of the surface 10 surrounding the limited area. Therefore, there is a high probability that cracks occur in the element 1 due to the large temperature difference. To prevent the occurrence of cracks, before the gas sensor with the element 1 is actually used for the engine in actual circumstances obtained when the engine is driven for a long time to move a vehicle, a testing method is performed for the element 1 in the same circumstances as the actual circumstances to confirm the reception of drops of water on the surface of the element 1.

To perform the testing method, a water confirming powder 2 formed of fine particles is prepared to be attached to the surface of the porous layer 100. In this preparation, fine particles having a melting point or a sublimation temperature equal to or higher than 1000° C. at the atmospheric pressure are used for the water confirming powder. The fine particles are not burned away even when the fine particles are exposed to the measured gas of 1000° C.

The water confirming powder 2 may have a specific color in a temperature range from 100 to 1000° C. The specific color is distinguishable from a color of the layer 100 of the element 1. That is, the powder 2 is not white, colorless or transparent, but colored. For example, the powder 2 is colored in red.

Further, fine particles of the powder 2 may be made of a material which is maintained in a solid state without being dissolved by any of water, lubricating oil and fuel oil. Moreover, fine particles of the powder 2 may be made of a material which is substantially not combined with a material of the layer 100 in a temperature range lower than a melting point of the material. That is, the fine particles of the powder 2 hardly react with the material of the layer 100.

Fine particles of the powder 2 may be formed to have diameters distributed in a range from 0.5 μm to 100 μm. In this case, traces of drops of water attached on the surface of the porous layer 100 can easily be confirmed. The reason is as follows. When fine particles of the powder 2 are distributed in a range from 0.5 μm to 100 μm, the fine particles can sufficiently be attached to a concave-convex surface of the porous layer 100. When the drops of water attached on the surface of the porous layer 100 is rapidly vaporized, the fine particles receiving the drops of water can sufficiently be sprung out or taken off from the surface by the vaporized water. As a result, traces of the drops of water attached to the surface can reliably be formed on the surface. Therefore, traces of drops of water attached on the surface of the porous layer 100 can easily be confirmed.

Assuming that fine particles of the powder 2 are distributed in a range smaller than 0.5 μm, fine particles not receiving but being placed around drops of water attached to the surface are also taken off from the surface, in addition to fine particles receiving the drops of water. Therefore, traces of the drops of water are hardly formed on the surface. In contrast, assuming that fine particles of the powder 2 are distributed in a range larger than 100 μm, it is difficult to sufficiently attach the powder 2 on the surface of the porous layer 100.

To measure an average diameter of fine particles of the powder 2, the powder 2 is mixed with water, and ultrasonic treatment is performed for agglomerate powder of the mixture for almost one minute to disperse fine particles of the powder 2 in the water. Then, an average diameter of the fine particles is measured with a laser diffraction type particle size distribution measuring device. As the device, a laser diffraction type microtrac (MT) particle size distribution measuring device (9320-X100 type) is, for example, used.

Preferably, fine particles of the powder 2 be formed to have diameters distributed in a range from 0.5 μm to 50 μm. Further, it is more preferable that fine particles having diameters ranging from 0.3 μm to 20 μm exist in the powder 2 when diameters of the fine particles are measured with a scanning electron microscope (SEM).

The heat treatment may be performed for the powder 2 of fine particles at a temperature equal to or higher than 1000° C. Therefore, even when the powder 2 is exposed to the measured gas of 1000° C., a change in quality and color of fine particles is prevented.

For example, iron oxide having a melting point higher than 1000° C. at the atmospheric pressure is used as a material of the powder 2. Particles of iron oxide are put into a mortar or the like and are pulverized to powder having diameters distributed in a range equal to or lower than 10 μm, so that a water confirming powder made of iron oxide is obtained.

This embodiment should not be construed as limiting to the iron oxide as a material of the powder 2. The powder 2 may be made of metal or metallic oxide having a melting point or a sublimation temperature equal to or higher than 1000° C. at the atmospheric pressure. For example, the powder 2 may be made of at least one of iron oxide, cobalt oxide, titanium oxide, nickel oxide, copper oxide, tungsten oxide, mica, agate, silicon, titanium, vanadium, chromium, manganese, iron, cobalt, nickel, copper, zirconium, molybdenum, tungsten, iridium, platinum, and gold. A meting point of tungsten is, for example, equal to 3380° C., and molybdenum has a melting point of 2623° C.

The testing method is described in detail with reference to FIGS. 1 to 3.

As shown in FIG. 1, the water confirming powder 2 of fine particles is uniformly applied on or attached to the whole surface of the porous layer 100 of the element 1 by using a brush (not shown). The powder 2 has the specific color distinguishable from a color of the surface of the porous layer 100 in a temperature range from 100 to 1000° C.

Then, the element 1 with the powder 2 is placed in a gas passage such that the powder 2 is exposed to the gas passage. In this case, the element 1 disposed in the gas sensor may be placed in the gas passage.

Then, a measured gas with moisture is caused to flow through the gas passage in predetermined conditions. Therefore, as shown in FIGS. 2 and 3, the element 1 receives drops 20 of water included in the measured gas on limited areas of the surface of the layer 100, while the drops 20 of water take out the powder 2 from the limited areas of the surface of the layer 100. Then, the drops 20 of water are vaporized while remaining traces of the drops 20 of water on the limited areas. No fine particles of the powder 20 are attached on the traces. The measured gas may be an exhaust gas output from an internal combustion engine of a vehicle or the like. The exhaust gas reaches a temperature of 1000° C. Even when the powder 2 is exposed to the exhaust gas of 1000° C., the powder 2 is adapted to maintain the specific color and the melting point or the sublimation temperature equal to or higher than 1000° C.

Then, the reception of the drops 20 of water on the surface of the layer 100 is confirmed. That is, the limited areas not coated with the powder 2 are observed by an operator's eye, and receiving conditions (positions, sizes and the like) of the drops 20 of water are measured and estimated. Therefore, the element 1 can be modified on the basis of the estimated receiving conditions so as to prevent the occurrence of cracks in the gas sensing element.

Therefore, because the water confirming powder 2 of fine particles has a melting point or a sublimation temperature equal to or higher than 1000° C., the powder 2 is not melted, sublimated or burned away even when the powder 2 is exposed to the measured gas of 1000° C. Therefore, when the powder 2 is exposed to the measured gas, the powder 2 can keep adhering to the surface of the layer 100 without being changed in shape, chemical properties or physical properties. Further, when the element 1 receives drops 20 of water in limited areas of the surface of the layer 100, confirmative traces of receiving the drops 20 of water can be reliably formed on the limited areas, and receiving conditions of the drops 20 of water can be measured and estimated.

Accordingly, the reception of the drops 20 of water can be confirmed in this testing method in the same circumstances as the actual circumstances obtained when the engine is actually driven to move a vehicle.

Further, because the water confirming powder 2 of fine particles has the specific color distinguishable from a color of the surface of the layer 100 in a temperature range from 100 to 1000° C., confirmative traces of the drops 20 of water formed on the surface of the layer 100 can be easily recognized by an operator's eye. However, the powder 2 may have the same color as that of the surface of the layer 100. In this case, confirmative traces of the drops 20 of water can be recognized by observing a difference in brilliance between the drops 20 of water and the powder 2 or observing a difference in components between the drops 20 of water and the powder 2 based on radiation of light having specific wavelengths.

Moreover, because an exhaust gas output from an internal combustion engine is used as the measured gas, the drops 20 of water can be received in the testing method in the same circumstances as the actual circumstances.

Furthermore, a small amount of lubricating oil and/or fuel oil mixed with water or the exhaust gas is received on the surface of the layer 100. However, because the powder 2 is maintained in a solid state without being dissolved by any of water, lubricating oil and fuel oil, the powder 2 not receiving any drop of water can reliably keep adhering to the surface of the layer 100. Accordingly, traces of the drops 20 of water can be accurately recognized.

Still further, fine particles of the powder 2 are made of a specific material which is substantially not combined with a material of the layer 100 in a temperature range lower than the melting point or the sublimation temperature of the powder 2. Accordingly, the powder 2 can reliably exist on the layer 100 without being changed in shape, chemical properties or physical properties.

Still further, because the fine particles of the powder 2 have diameters distributed in a range equal to or lower than 10 μm, the powder 2 can sufficiently adhere to the surface of the layer 100.

Still further, the heat treatment is performed in advance for the powder 2 at a temperature equal to or higher than 1000° C. Accordingly, even when the powder 2 is exposed to the measured gas of 1000° C., a change in quality and color of the powder 2 can be prevented.

Still further, fine particles of the powder 2 are made of metal or metallic oxide. Accordingly, the powder 2 can be stably maintained even when the powder 2 is exposed to the exhaust gas of 1000° C. Further, a change in color or size of the powder 2 can be reliably prevented, so that traces of drops of water on the surface of the layer 100 can be correctly formed. Moreover, fine particles of the powder 2 having small diameters can be easily obtained.

Still further, because the porous layer 100 having a rough outer surface is disposed on the surface 10 of the element 1, the powder 2 can be sufficiently attached to the surface of the porous layer 100.

In the testing method, after the powder 2 is attached to the surface of the layer 100, air may slightly be blown against the surface of the layer 100 to blow off a portion of the powder 2 excessively adhering to the surface of the layer 100. Therefore, the powder 2 uniformly adhering to the surface of the layer 100 can be reliably obtained.

Further, a thermo couple (not shown) may be attached to the element 1 to measure a temperature of the surface 10 of the element 1. In this case, the operation of the heater 14 is controlled such that the temperature of the surface 10 of the element 1 is, for example, maintained at 700° C.

Moreover, the porous layer 100 has a rough surface, so that the powder 2 can be easily attached to this rough surface. However, the powder 2 may be directly applied on or attached to the surface 10 of the element 1 without disposing the porous layer 100 in the element 1. In this case, it is preferred that the surface 10 of the element 1 is roughed so as to have the roughness Rz of 5 μm or more. That is, the surface 10 of the element 1 is roughed so as to have concave and convex portions at intervals of 5 μm or more.

Furthermore, the powder 2 is attached to the surface of the element 1. However, the element 1 may be immersed in slurry wherein fine particles of the powder 2 are mixed with solvent.

Embodiment 2

In this embodiment, a method of estimating a volume of a drop of water is described.

To examine a relation between a volume of a drop of water received on the surface of the layer 100 and a diameter of the drop of water, experiments were performed for the element 1. In these experiments, the heater 14 was controlled so as to maintain the temperature of the surface 10 of the element 1 at 700° C. Then, water was dropped on the surface of the layer 100, and a volume of each drop of water and a diameter of the drop of water were measured. Experimental results are shown in FIG. 4.

Figure 4:
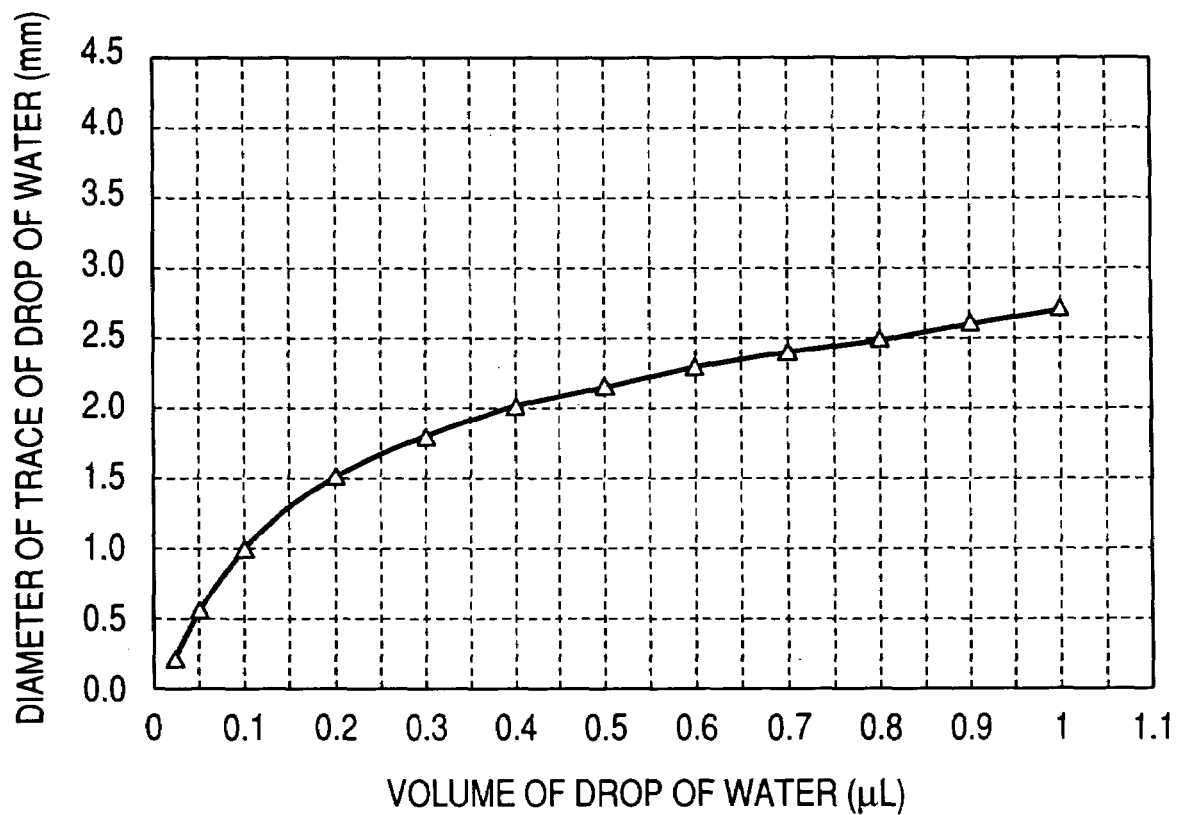
FIG. 4 is a view showing a relation between a volume of a drop of water received on a surface of the gas sensing element and a diameter of the drop of water, according to the second embodiment of the present invention.

As shown in FIG. 4, when a volume of a drop of water is equal to 0.2 micro litters (μl), a diameter of a trace formed by the drop of water is 1.5 mm. When a volume of a drop of water is equal to 0.4 μl, a diameter of a trace formed by the drop of water is 2.0 mm. Therefore, it is realized that, as the volume is increased, the diameter becomes larger.

Accordingly, a volume of a drop of water can be estimated from a diameter of a trace formed by the drop of water.

Although it is assumed that the relation between the volume and diameter is changed with the temperature of the surface 10 of the element 1, it would be realized that the diameter becomes larger with the volume regardless of the temperature of the surface 10 of the element 1.

What is claimed is:

1. A method of confirming reception of a drop of water in a gas sensing element for detecting a concentration of a specific component included in a measured gas, comprising the steps of:
    applying a powder on a surface of the gas sensing element;
    placing the gas sensing element in a gas passage so as to expose the surface of the gas sensing element to the gas passage;
    causing the measured gas to flow through the gas passage;
    receiving a drop of water included in the measured gas on a limited area of the surface of the gas sensing element such that the drop of water takes out the powder from the limited area; and
    confirming the reception of the drop of water on the surface of the gas sensing element, based on a trace of the drop of water at which the powder is taken out,
    wherein the powder has a melting point or a sublimation temperature equal to or higher than 1000° C.

2. The method according to claim 1, further comprising a step of forming the powder having a specific color distinguishable from a color of the surface of the gas sensing element in a temperature range from 100 to 1000° C.

3. The method according to claim 1, further comprising the steps of:
    forming the powder having a specific color distinguishable from a color of the gas sensing element in a temperature range from 100 to 1000° C. and having the melting point or the sublimation temperature equal to or higher than 1000° C. in circumstances that the powder is exposed to an exhaust gas output from an internal combustion engine; and
    using the exhaust gas as the measured gas.

4. The method according to claim 1, further comprising a step of forming fine particles of the powder which are maintained in a solid state without being dissolved by any of water, lubricating oil and fuel oil.

5. The method according to claim 1, further comprising a step of forming fine particles of the powder which are substantially not combined with a material of the gas sensing element in a temperature range lower than the melting point or the sublimation temperature of the powder.

6. The method according to claim 1, further comprising a step of forming fine particles of the powder which have an average diameter distributed in a range from 0.5 μm to 100 μm.

7. The method according to claim 1, further comprising a step of performing heat treatment for the powder at a temperature equal to or higher than 1000° C.

8. The method according to claim 1, further comprising a step of forming fine particles of the powder made of metal or metallic oxide.

9. The method according to claim 1, further comprising a step of forming fine particles of the powder made of at least one of iron oxide, cobalt oxide, titanium oxide, nickel oxide, copper oxide, tungsten oxide, mica, agate, silicon, titanium, vanadium, chromium, manganese, iron, cobalt, nickel, copper, zirconium, molybdenum, tungsten, iridium, platinum, and gold.

10. The method according to claim 1, further comprising a step of forming a porous layer on the surface of the gas sensing element so as to apply the powder on a surface of the porous layer in the step of applying the powder.

11. The method according to claim 1, further comprising the steps of:
  forming a surface portion of the gas sensing element made of a ceramic material.

12. The method according to claim 1, wherein the step of confirming the reception of the drop of water includes:
  measuring a diameter of the drop of water; and
  estimating a volume of the drop of water from the diameter.

* * * * *